US006331254B1

(12) United States Patent
White et al.

(10) Patent No.: US 6,331,254 B1
(45) Date of Patent: Dec. 18, 2001

(54) METHODS OF SEPARATION AND DETECTION

(75) Inventors: Thayer White, Clyde Hill; Edward Nudelman, Seattle, both of WA (US)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

(21) Appl. No.: 09/465,678

(22) Filed: Dec. 17, 1999

Related U.S. Application Data

(63) Continuation-in-part of application No. 09/049,941, filed on Mar. 30, 1998, now abandoned, and a continuation of application No. PCT/US99/06803, filed on Mar. 30, 1999.

(51) Int. Cl.⁷ .................................................. B01D 15/08
(52) U.S. Cl. ...................... 210/658; 210/198.3; 436/162; 436/172
(58) Field of Search .................................... 210/635, 656, 210/658, 198.2, 198.3; 436/161, 162, 172, 174

(56) References Cited

U.S. PATENT DOCUMENTS

| 3,832,134 | 8/1974 | Sohn ................................. 23/230 B |
| 4,292,041 | 9/1981 | Fullerton ............................. 23/230.3 |
| 5,879,528 | 3/1999 | Yeung et al. ......................... 204/452 |

FOREIGN PATENT DOCUMENTS

| 1051421 | 7/1982 | (SU) ..................................... 210/658 |
| 1402943 | 6/1988 | (SU) ..................................... 210/658 |
| 1430888 | 10/1988 | (SU) ..................................... 210/658 |

OTHER PUBLICATIONS

Kester et al.; "Interleukin–1 Generates Transmemorane Signals from Phospholipids Through Novel Pathways in Cultured Rat Mesangial Cells"; The Journal of Clinical Investigations; Feb. 1989; vol. 83, No. 2; pp. 718–723.

West et al.; "Cloning and Expression of Two Human Lysophosphatidic Acid Acyltransferase cDNAs That Enhance Cytokine–Induced Signaling Responses in Cells"; DNA and Cell Biology; Jun. 1997; vol. 16, No. 6; pp. 691–701.

Musial et al.; "Interleukin–1 and Endothelin Stimulate Distinct Species of Diglycerides That Differentially Regulate Protein Kinase C in Mesangial Cells"; The Journal of Biological Chemistry; Sep. 15, 1995; vol. 270, No. 37; pp. 21632–21638.

Mandal et al.; "Interleukin–1–induced Ether–Linked Diglycerides Inhibit Calcium–Insensitive Protein Kinase C. Isotypes"; Journal Biology Chemistry; 1997; vol. 272, No. 32; pp. 20306–20311.

Lavie et al.; "Accumulation of Glucosylceramides in Multidrug–Resistant Cancer Cells"; The Journal of Biological Chemistry; vol. 271; No. 32; Aug. 9, 1996; pp. 19530–19536.

English et al.; "Messenger Functions of Phosphatidic Acid". Chem. Physics of Lipids, 1996; vol. 80; pp. 117–132.

Mathias et al.; "Ceramide: A Novel Second Messenger"; Advances in Lipid Research; 1993; vol. 25; pp. 65–89.

(List continued on next page.)

*Primary Examiner*—Ernest G. Therkorn
(74) *Attorney, Agent, or Firm*—Foley & Lardner (57) ABSTRACT

Methods which employ thin layer chromatography for separating and detecting hydrophobic target molecules are particularly useful in separating biologically relevant lipids. By utilizing non-destructive detection techniques, these methods also can be adapted to further quantification or structural analysis.

18 Claims, 4 Drawing Sheets

OTHER PUBLICATIONS

Hannum et al.; "The Novel Second Messenger Ceramide: Identification, Mechanism of Action, and Cellular Activity"; Advances in Lipid Research; 1993; vol. 25; pp. 43–64.

English et al.; "Phosphatidic Acid: A Lipid Messenger Involved in Intracellular and Extracellular Signalling"; Cell Signal; 1996; vol. 8. No. 5; pp. 341–347.

Boarder; "A role fro Phospholipase D in control of Mitogenesis"; TiPS, 1994; vol. 15; pp. 57–61.

BI, K. et al.; "Phosphatidic acid formation by phopholipase D is required for transport from the endoplasmic reticulum to the Golgi complex"; Current Biology; 1997; vol. 7, No. 5; pp. 301–307.

Mollinedo et al.; "Involvement of Phospholipase D in the Activation of Transcription Factor AP–1 in Human T Lymphoid Jurkat Cells"; J. Immunology; 1994; vol. 153; pp. 2457–2462.

Rice, G. C. et al.; "Protection from endotoxic shock in mice by pharmacologic inhibition of phosphatidic acid"; Proc. Natl. Acad. Sci. USA; 1994; vol. 91; pp. 3857–3861.

Bursten et al.; "Interleukin–1 Rapidly Stimulates Lysophosphatidate Acyltransferase and Phosphatidate Phosphohydrolase Activities in Human Mesangial Cells"; J. Biol. Chem., 1991; vol. 266, No. 31; pp. 20732–20743.

Bursten et al.; "Interleukin–1 stimulates phosphatidic acid–mediated phospholipase D activity in human mesangial cells"; Cell Physiol., 1994; vol. 35; pp. C1093–C1104.

Wen et al.; "Lipid signal transduction pathways in angiotensin II type 1 receptor–transfected fibroblasts"; Amer. J. Physiol.; 1995; vol. 269 (Cell Physiol., vol. 38); pp. C435–C442.

Flores et al., "Phosphatidic Acid Generation through Interleukin 2 (IL–2)–induced α–Diacylglycerol Kinase Activation Is an Essential Step in IL–2–mediated Lymphocyte Proliferation"; J. Biol. Chem.; 1996; vol. 271, No. 17; pp. 10334–10340.

Eardley et al., "Glycosylphosphatidylinositol: A Candidate System for Interleukin–2 Signal Transduction"; Science; 1991; vol. 251; pp. 78–81.

Booz et al.; "Angiotensin II induces phosphatidic acid formation in neonatal rat cardiac fibroblasts: Evaluation of the roles of phospholipases C and D"; Mol. and Cell. Biochem.; 1994; vol. 141; pp. 135–143.

Huterer et al.; "Metabolism of bis(monoacylglycero)phosphate in macrophages"; J. Lipid Res.; 1979; vol. 20; pp. 966–973.

Holbrook et al.; "Bis(monoacylglycero)phosphate from PC12 cells, a phospholipid that can comigrate with phosphatidic acid: molecular species analysis by fast atom bombardment mass spectrometry"; Biochimica et Biophysica Acta; 1992; vol. 1125; pp. 330–334.

Van Blitterswijk et al., "Rapid attenuation of receptor–induced diacylglycerol and phosphatidic acid by Phospholipase D–mediated transphosphatidylation: formation of bisphosphatidic acid"; EMBO J.; 1993; vol. 12; pp. 2655–2662.

Bursten et al.; "Interleukin–1 Rapidly Stimulates Lysophosphatidate Acyltransferase and Phosphatidate Phosphahydrolase Activities in Human Mesangial Cells"; J. Biol. Chem.; 1991; vol. 266, No. 31; pp. 20732–20743.

Bursten et al.; "Potential Role for Phosphatidic Acid in Mediating the Inflammatory Responses to TNFαand IL–1β"; Circulatory Shock; 1994; vol. 44; pp. 14–29.

MOD-Neutral TLC

FIG. 2B

MOD-FF TLC

FIG. 3

METHODS OF SEPARATION AND DETECTION

REFERENCE TO RELATED APPLICATIONS

This application is a continuation-in-part of Ser. No. 09/049,941, filed Mar. 30, 1998, now abandoned and a continuation of PCT/US99/06803 filed Mar. 30, 1999.

BACKGROUND OF THE INVENTION

Classical planar thin layer chromatography (TLC) was introduced over 50 years ago. Izmailov et al., Farmatsiya 3, 1 (1938). Planar TLC is the method of choice for the separation and isolation of many classes of lipid compounds, especially those found in mammalian cell membranes: glycosphingolipids, phospholipids, neutral glycerol derivatives containing acyl chains such as triglycerides and diglycerides, and cholesteryl esters.

Recent advances in TLC, especially with regard to the reduction in, and uniformity of, silica particle size and the uniformity of plate coating, have led to the production of high performance TLC plates which significantly enhance separations of analytes. But the current TLC methods are problematic both in quantification and in analyzing significant mass changes in multiple samples of smaller cellular lipids, such as phosphatidic acid (PA) and diradylglycerols (DG). Conventional methods simply lack high-throughput capability.

Although historically important by virtue of their role in membrane formation, lipids have become the focus of interest more recently for a variety of physiologically important reasons. For example, recent interest in PA and DG has been piqued by the discovery that they play important roles in cellular signaling. See, for example, English et al., Chem. Physics of Lipids 80, 117–132 (1996); Mathias et al., Advances in Lipid Research 25, 65–89 (1993); and Hannun et al., loc. cit. 43–64 (1993). PA species, for example, have been implicated in mitogenesis, cellular transformation, and exocytic processes. See English, Cell Signal 8, 341–347 (1996), and Boarder, Trends in Pharmacological Sciences, 15, 57–61 (1994). PA species also have been implicated in inflammatory signaling by Interleukin-1 (IL-1). Bi et al., Current Biology 7, 301–307 (1997). In addition, many different enzymes which regulate PA cellular concentration, are strongly associated with signaling by cell activators, including Lipid A and the cytokines IL-1 and IL-2. See Mollinedo et al., J. Immunol. 153, 2457–2462 (1994); Rice et al., Proc. Nat'l Acad. Sci USA 91, 3857–3861 (1994); and West et al., DNA and Cell Biology 16, 691–701 (1997). Among such enzymes are lyso-PA acyl CoA: acyltransferase (LPAAT), phosphatidate phosphohydrolase (PAP), diacylglycerol kinase (DG kinase), and phosphatidylcholine-directed phospholipase D (PC-PLD). The measurement of the substrates and products of these enzymes directly correlate to a physiological state.

DG species have been implicated in cell activation through protein kinase C (PKC) signaling, or otherwise regulating calcium-sensitive PKC isotypes, respectively. Musial et al., J. Biol. Chem. 270, 21632–21638 (1995); Baldi et al., J. Applied Physiol. 217, 356–365 (1994); Kester et al., J. Clin. Invest 83, 718–723 (1989); and Mandal et al., J. Biol. Chem 272, 20306–20311 (1997). DG participation in a variety of separable cellular synthetic pathways, like PA, has been implicated in different inflammatory processes. Mandal et al., J. Biol. Chem 272, 20306–20311 (1997), and Bursten et al., loc. cit. 266, 20732–20743 (1991).

It has become of increasing interest, therefore, to measure changes in mass in these lipid species and to isolate them for resolution and identification of component species and subspecies, such as by gas chromatographic analysis of acyl chain composition and/or mass spectrometry. Bursten et al., J. Biol. Chem. 266, 20732–20743 (1991); Rice et al., Proc. Nat'l Acad. Sci 91, 3857–3861 (1994); and Lavie et al., J. Biol. Chem. 271, 19530–19536 (1996).

Previous separation methods have not been adequate, however, to demonstrate an origin and/or acyl composition of these critical lipid species. These failings include: destructive detection methods which result in an inability to perform serial analyses; insufficient concentrations of lipids because of poor detection limits; and labeling methods which are insensitive and not specific enough, which leads to ambiguous, if not erroneous results.

Two-dimensional TLC systems are sometimes satisfactory for the separation of complex mixtures of lipids, but none allows for examination of multiple samples on the same plate. The use of one-step (single resolution) TLC systems permits the analysis of multiple samples, but lacks the ability to separate complex mixtures. TLC analysis of phospholipids such as PA also has heretofore lacked the ability to separate congeners of PA such as lyso(bis) PA, cardiolipin, (bis)PA, and/or phosphatidylglycerol, or has been frustrated by the small amounts of PA present or generated in different cell types. See Bursten et al., Cell Physiol. 35, C1093–C1104 (1994); Wen et al., Amer. J. Physiol 269 (Cell Physiol 38) C435–C442 (1995); Flores et al., J. Biol. Chem. 271, 10334–10340 (1996); Eardley et al., Science 251, 78–81 (1991); Musial et al., J. Biol. Chem. 270, 21632–21638 (1995); Booz Molecular and Cellular Biochemistry 141, 135–143 (1994); Huterer et al., J. Lipid Research 20, 966–973 (1979); Pannell et al., Biochimica et Biophysica Acta 1125, 330–334 (1992); and van Blitterswijk, EMBO J. 12, 2655–2662 (1993).

Previous quantification techniques typically have relied upon less sensitive TLC techniques. Some of these poor techniques, in turn, have depended upon radioactive labeling of cells using either selected acyl chains, such as $^{14}C$-myristate, or alkyl lyso-phospholipids, for example, $^{14}C$-alkyl-lyso-PC. Aside from the obvious radioactivity hazard and an inability to use such samples in mass determinations, such methods also are problematic. Labeling of cells with myristate, for example, works on the assumption of selective labeling of phosphatidylcholine, which may contain the bulk of myristate but may not be the source of PA, rendering such analysis irrelevant. Bursten et al., Cell Physiol. 35, C1093–C1104 (1994), and Eardley et al., Science 251, 78–81 (1991). In addition, selective labeling of PC with alkyl-lyso-PC may identify activation of PC-PLD, but it cannot identify simultaneous activation of the other PA-generating enzymes, such as DG kinase or LPAAT (9, 13, 20, 24, 30, 31). Bursten et al., J. Biol. Chem. 266, 20732–20743 (1991); Rice et al., Proc. Nat'l Acad. Sci USA 91, 3857–3861 (1994); Lavie et al., J. Biol. Chem. 271, 19530–19536 (1996); Bursten et al., Circulatory Shock 44, 14–29 (1994); Flores et al., J. Biol. Chem. 271, 10334–10340 (1996); and Eardley et al., Science 251, 78–81 (1991).

Many methods also rely on HPLC separation of cellular phospholipids. HPLC separation of phospholipids is confounded, however, by the tendency of PA to separate widely on silica columns by acyl and/or alkyl/alkenyl composition, but then co-migrate with similarly composed PA congeners such as cardiolipin. For example, dilinoleoyl PA is known to comigrate with cardiolipin, due to significant linoleoyl content of the latter. This necessitates serial gradient HPLC separations resulting in significant loss of mass, or requires very large, sometimes prohibitive, sample sizes to demonstrate significant lipid changes. Wen et al., Amer. J. Physiol 269 (Cell Physiol 38), C435–C442 (1995). These methods are expensive, inefficient, and cannot be applied to dose-responses, time courses, or other comparisons which must generate multiple data points for analyses in parallel.

A need exists, therefore, for a method facilitating the rapid, sensitive, and quantitative simultaneous resolution and detection of multiple biologically relevant molecules under a variety of conditions on the same plate, while maintaining lipid integrity for further analysis. This need encompasses improvement of methods for quantification of cellular lipids, including rare species of biologically-active cellular lipids, such as PA and DG. These methods should render lipids amenable to further analysis of hydrolyzed acyl chains by methods such as gas chromatography, which requires high quality separation. Importantly, these methods should be susceptible to high-throughput.

SUMMARY OF THE INVENTION

Among the objects of the invention, therefore, are providing a high-throughput TLC system for the rapid, sensitive and quantitative separation and detection of essentially hydrophobic molecules of biological import. Another object of the invention is to provide a TLC system which is capable of simultaneously resolving multiple samples on a single TLC plate.

It is yet another object of the invention to provide non-destructive TLC methods of separation and detection that allow the subsequent further characterization of the molecule being separated.

According to these objects, a method of separating and detecting an essentially hydrophobic molecule is provided which comprises providing a sample; separating the molecule of interest by thin layer chromatography (TLC) utilizing multiple resolutions in the same direction and dimension, with the mobile phases selected from chloroform-methanol-acetic acid/ammonium hydroxide, hexane-diethylether-acetone, hexane-diethylether and 100% hexane; and detecting the separated molecular component.

Also according to these objects of the invention, a method is provided for separating and detecting an essentially hydrophobic molecule which comprises providing a sample; separating the molecule of interest by TLC at least once in one direction in one dimension at least once, following separation at least once more in the same dimension, but in the opposite direction, using mobile phases selected from hexane-diethylether-acetone or chloroform-methanol-ammonium hydroxide-water and chloroform-methanol-acetic acid-water; and detecting the separated molecule.

According to this and other objects of the invention, a TLC method is provided which utilizes a non-destructive detection agent.

ABBREVIATIONS USED

The abbreviations used in this disclosure include: TLC, thin layer chromatography; CE, cholesteryl ether; TAG, triacylglycerol; FFA, free fatty acid; DG, diradylglycerol; Chol, cholesterol; FAB-MS, fast-atom bombardment mass spectrometry; MAG, monoacylglycerol; Cer, ceramide; PA, phosphatidic acid; PE, phosphatidyl ethanolamine; PC, phosphatidyl choline; PA, phosphatidic acid; PI, phosphatidyl inositol; PS, phosphatidyl serine; PBS, phosphate-buffered saline.

BRIEF DESCRIPTION OF THE DRAWINGS

FIG. 1 shows the separation achieved using the inventive TLC system to separate CE, TAG, FFA, DG, Chol, and MAG.

DETAILED DESCRIPTION OF THE PREFERRED EMBODIMENT

The inventive methods derive from the discovery of a simple, non-destructive method of separating and detecting essentially hydrophobic molecules. The basic methods utilize high performance TLC (HPTLC) media, but conventional thin layer chromatography (TLC) matrices also may be used. The present methods are particularly suitable for the separation of lipids, and most preferably lipids of biological origin/significance. Owing to their similar chemical properties, peptides, oligosaccharides and drugs (e.g., lisofylline) having charge distributions and hydrophobic character similar to biological lipids also may be separated and detected and quantified by the subject methods. Although the basic methods involve separation, detection and quantification, the same techniques, because of their non-destructive nature, may be applied to further structural analysis of the molecules subject to these methods. Thus, methods of isolation and structural determination also are contemplated.

The Sample

In all embodiments of the basic method, a sample is provided which contains a molecule of interest ("target molecule"), which is to be separated and detected. The target molecule can be any molecule which has physical properties (e.g., hydrophobic and/or ionic properties) similar to the molecules exemplified below. Although usually a lipid, the target molecule can include, for example, lipid soluble vitamins (e.g. vitamins D and E). Other target molecules include peptides, amino acids, organic compounds, oligosaccharides and certain drugs, especially methylxanthines like lisofylline.

The basic method is especially suitable for the separation of biological lipids.

The great variety of biological lipids are known to those of ordinary skill. Some examples include lipids associated with cell membranes, lipoproteins (e.g., high density, low density and very low density lipoproteins), hormones (e.g. steroids, such as glucocorticoids, estrogens and androgens), and those linked to cellular signaling pathways (e.g. ceramide).

Some lipids of particular interest include phospholipids, like phosphatidyl glycerol, phosphatidyl inositol and cardiolipin, glycolipids, and sterols, such as cholesterol, and derivatives of these. Glycerol lipids, sulfolipids and sphingolipids are also of interest. Specific non-limiting examples include cholesteryl ester (CE), triacylglycerol (TAG), free fatty acid (FFA), diradylglycerol (DG), cholesterol (Chol), monoacylglycerol (MAG), phosphatidyl ethanolamine (PE), phosphatidyl choline (PC), phosphatidyl serine (PS), phosphatidyl inositol (PI), phosphatidic acid (PA) and lysophospholipid derivatives thereof. Diradylglycerols include both ester linked in the sn-1 and sn-2 positions (diacylglycerols:DAG; monoacylglycerols) and ether-linked in the sn-1 and sn-2 positions (alkyl, acylglycerols: AAG; alkenyl, acylglycerols). Because of their involvement in cellular signaling, lipids of great interest are those physiologically associated with (e.g. products and substrates) the activity of an enzyme selected from the group consisting of lyso-PA acyl CoA acyltransferase (LPAAT), phosphatidate phosphohydrolase (PAP or PAPH), diacylglycerol kinase (DG kinase), protein kinase C and phosphatidylcholine-directed phospholipase D (PC-PLD). Obviously, other molecules, especially peptides, having properties similar to these lipid species are quite adaptable to separation and detection according to the inventive methods.

Because of the variety of molecules that may be separated and detected according to the present methods, the source material for the sample may vary widely. Although animal sources are quite suitable, plant, bacterial and fungal sources may also be used. For biomedical and veterinary applications a preferred sample source is the blood. Of course tissue samples also may be used, but they typically will require greater manipulation before being amenable to the present separating and detecting. Thus, when blood samples are used, either the cellular or, preferably, the serum or plasma component may be used. This preference is based, however, on ease of manipulation. If cell membrane-associated lipids were of interest, for example, the cellular component would be used. In applications, like basic science applications, where ease of preparation is not as important, any component of virtually any organism may be used. Additional bodily fluids of interest include saliva, mucous, sperm and sweat. In addition to normal tissues, dysplastic, preneoplastic and neoplastic samples are also envisioned as useful.

Prior to engaging the present methods, the molecule to be separated and detected must be reduced to a form suitable for TLC application. In other words, the molecule typically must be dissolved, or at least suspended, in a suitable solvent. Most samples, therefore, will require some sort of extraction treatment. Where tissue samples or samples from organisms having cell walls are of interest, some type of mechanical or chemical disruption is useful. Suitable means are well known in the art and include, for example, the use of a tissue homogenizer or a French pressure cell in conjunction with, for example, organic solvent extractions. Methods of cell disruption and fractionation can be found in books such as CURRENT PROTOCOLS IN MOLECULAR BIOLOGY, Ausubel et al., eds. (John Wiley & Sons 1997). Most usually samples will be extracted with solvents having varying hydrophobic properties. The optimal solvent will depend upon the nature of the molecule of interest. Such extractions also are conventional in the art and any technique which results in a sample suitable for application to a TLC plate is useful in the present methods.

One such non-limiting extraction technique can be performed according to the method disclosed by Dole et al., *J. Clin. Invest.* 35: 150–54 (1956), and Dole et al., *J. Biol. Chem.* 235: 2595–99 (1960). Briefly, this method involves sequential extractions of the sample with an isopropanol/heptane/sulfuric acid mixture and multiple heptane extractions. The final organic phase is dried under nitrogen for use in subsequent processing steps.

Additional extraction techniques are described in Bligh et al., *Canadian J. Biochem. Physiol.* 37: 914–17 (1959), and Folch et al., *J. Biochem.* 226: 497–509 (1957). The method of Bligh et al. involves an organic extraction of lipids from biological tissue homogenates or fluids. Briefly, samples are extracted with methanol-chloroform, chloroform, filtered and back-extracted with water. The method of Folch et al. involves the extraction of lipids from biological tissue homogenates or body fluids. Briefly, samples are extracted with chloroform-methanol, filtered and back-extracted with 0.1 N KCl. Further exemplary methods are provided below in the Examples.

Separation

Although TLC, including HPTLC, is well known, in one aspect of the present method, it differs markedly from prior methods in its ability effectively to separate target molecules, especially biological lipids. This advantage is due, at least in part, to the combination of multiple resolutions in a single dimension and the specific solvents utilized.

For example, once a sample is provided, it is applied to a TLC (or HPTLC) plate and preferably dried. Separation in one aspect of the invention is accomplished by resolving the target molecule in one direction in one dimension, followed by resolving said lipid at least a second time in the same direction and same dimension, i.e., multiple one dimensional TLC (MOD-TLC). In another aspect of the invention, the multiple one dimensional separation is used, except that in this aspect at least one resolution is performed in the opposite direction, still in the same dimension. This second aspect is referred to MOD-Flip-Flop TLC (MOD-FF TLC), since it can be accomplished by turning the TLC plate 180° between resolutions.

Unlike two dimensional techniques, changing the orientation of the plate is unnecessary in MOD-TLC. This gives rise to the advantage of being able to run many samples on a single TLC plate, in contrast to the single-sample capacity of two dimensional TLC. Moreover, given that the only mechanical manipulation required during the run is a solvent change, this method is quite adaptable to automation.

For clarity it should be noted that when the name of a mobile phase specifies the presence of an ingredient, that ingredient is present in an amount greater than 0%. If the name of a mobile phase specifies two ingredients separated by a slash (/), the ingredients on either side of the slash are present in the alternative, i.e. only one is present at a time. In addition, unless otherwise indicated, all proportions and percentages in reference to a mobile phase are expressed relative to volume.

In MOD-TLC, the mobile phase in the first resolution usually contains chloroform-methanol-acetic acid/ammonium hydroxide. The exact composition of this mobile phase can be adapted to the molecule of interest. In some cases, it may be useful to use the additional mobile phases discussed below as a first mobile phase. The most effective chloroform-methanol-acetic acid/ammonium hydroxide mobile phases contain at least about 80% (v/v/v) chloroform. In resolving lipids especially, the chloroform-methanol-acetic acid/ammonium hydroxide mobile phase can contain from about 86% to about 94% (v/v/v) chloroform, from about 8% to about 12% (v/v/v) methanol and/or less than about 2% acetic acid or concentrated ammonium hydroxide. The composition of one particularly useful chloroform-methanol-acetic acid/ammonium hydroxide mobile phase is 90:10:1 (v/v/v).

The mobile phase of the second (and optional additional) resolution(s), which may also be used in the first resolution, is comprised of hexane-diethylether-acetone, hexane-diethylether or 100% hexane. Depending upon the nature of the target molecule, the chloroform-methanol-acetic acid mobile phase, above, also may be used in the second resolution. The hexane-diethylether-acetone mobile phase should contain at least about 55% hexane (v/v/v). In resolving lipids especially, the hexane-diethylether-acetone mobile phase typically contains from about 57% to about 63% hexane (v/v/v), between about 35% and about 45% diethylether (v/v/v), and/or from about 3% to about 7% (v/v/v) acetone. The composition of one particularly useful hexane-diethylether-acetone mobile phase is 60:40:5 (v/v/v).

The hexane-diethylether mobile phase should contain at least about 93% (v/v) hexane. In resolving lipids especially, the hexane-diethylether mobile phase typically contains between about 91% and about 95% (v/v) hexane and/or between about 1% and about 7% (v/v) diethylether. The composition of one particularly useful hexane-diethylether mobile phase is 97:3 (v/v).

In one embodiment of MOD-TLC, a chloroform-methanol mobile phase is used in the first resolution and a hexane-diethylether-acetone mobile phase is used in the second resolution. In a preferred embodiment, a third resolution is performed, wherein the mobile phase in the third resolution is a hexane-diethylether mobile phase. In a most preferred embodiment, a fourth resolution is undertaken using a 100% hexane mobile phase. This preferred embodiment is termed MOD-Neutral TLC.

As discussed above, MOD-FF TLC involves multiple one dimensional resolution, incorporating at least one resolution in the opposite direction. Although the foregoing solvent systems may sometimes be useful in the Flip-Flop version, preferred solvent systems include combinations of hexane-diethylether-acetone, chloroform-methanol-ammonium hydroxide-water and chloroform-methanol-acetic acid-water. Typically, hexane-diethylether-acetone mobile phases contains at least about 50% (v/v/v) hexane. A particularly useful hexane-diethylether-acetone mobile phase for separating lipids contains between about 56% and about 64% (v/v/v) hexane, from about 36% to about 44% (v/v/v) diethylether and/or from about 7% to about 3% (v/v/v) acetone. One preferred hexane-diethylether-acetone mobile phase is 60:40:5 (v/v/v)

A useful chloroform-methanol-ammonium hydroxide-water mobile phase contains at least about 50% chloroform (v/v/v/v). In separating lipids, a very good chloroform-methanol-ammonium hydroxide-water mobile phase contains from between about 56% and about 64% (v/v/v/v) chloroform, from about 50% to about 56% (v/v/v/v) methanol, between about 3% and about 5% (v/v/v/v) ammonium hydroxide, and/or less than about 2% water. One quite useful chloroform-methanol-ammonium hydroxide-water mobile phase is 60:53:4:1 (v/v/v/v).

A useful chloroform-methanol-acetic acid-water mobile phase contains at least about 75% (v/v/v/v) chloroform. For lipid separation, a useful chloroform-methanol-acetic acid-water mobile phase contains between about 82% and about 88% (v/v/v/v) chloroform, from about 12% to about 13% methanol, about 12% to about 13% acetic acid, and/or less than about 5% water. A very useful chloroform-methanol-acetic acid-water mobile phase is 85:12.5:12.5:3 (v/v/v/v).

In one embodiment, a hexane-diethylether-acetone mobile phase is used in the first resolution and a chloroform-methanol-ammonium hydroxide-water mobile phase is used in the second resolution. In a preferred embodiment, a third resolution is performed, wherein the mobile phase in the third resolution is a chloroform-methanol-acetic acid-water mobile phase. In a most preferred embodiment, the first two resolutions are undertaken in the same direction and dimension, but the third resolution, while being in the same dimension, is performed in the opposite direction, i.e., 180°, from the first and second resolutions. Subsequent to the resolution in the opposite direction, the plate can be broken to remove species that may interfere with the separation of the species of interest.

In another embodiment, which is useful, for example, in the separation of PI from PC, a first resolution is carried out using a mobile phase containing, for example, about 65:30:4 (v/v/v) chloroform-methanol-ammonium hydroxide. Following this first resolution, PC that has separated from PI is detected and the TLC plate is broken below the separated PC. This prevents comigration of PC and PI. The portion of the TLC plate not containing PC is then flipped 180° and a second and third resolution are performed, which, while in the same dimension as the first resolution, are in the opposite direction due to the flipping of the TLC plate. The mobile phase of the second resolution contains, for example, about 70:30:15:6 (v/v/v/v) chloroform-methanol-acetic acid—water. The mobile phase of the third resolution contains, for example, about 85:12.5:12.5:3 (v/v/v/v) chloroform-methanol-acetic acid-water. Optionally, following the third resolution, a fourth resolution can be carried out. The fourth resolution is carried out in the same dimension and direction as the second and third resolutions and with a mobile phase, which, like the mobile phase of the third resolution contains, for example, about 85:12.5:12.5:3 (v/v/v/v) chloroform-methanol-acetic acid-water.

As with conventional TLC, the time of each resolution will depend upon the nature of the target molecule. Obviously, however, when multiple resolutions are performed the time should not exceed that required for the target molecule to develop to the end of the TLC plate. Hence, in a typical method a development time should be chosen such that the target molecule migrates a suitable distance so as to allow further single or multiple resolutions. Depending on the characteristics of the molecule of interest, the sample may be resolved additional times (preferably 3–5 times total) in the same dimension. Optimal resolution is obtained by changing the solvent composition between each resolution. It is usually beneficial also to dry the plate between resolutions.

With regard to the mobile phases described herein containing acetic acid and/or ammonium hydroxide, the concentration of these chemicals, as is well known to the skilled artisan, should be sufficient to effectuate the desired protonation or deprotonation of the sample constituents. A preferred concentration of acetic acid is glacial acetic acid. A preferred concentration of ammonium hydroxide is 28% to 30% ammonia ($NH_3$) in water.

Detection

Usually, but not necessarily, following separation the target molecule is detected. Although the many known methods of detecting lipids in TLC systems may be applied to the inventive methods, non-destructive methods are preferred. Thus, in one aspect of the invention, the target molecule is treated with a non-destructive agent that associates with the target molecule and facilitates detection. This treatment typically is done after the separation, but it is possible to derivatize (as above) the target molecule prior to separation and this may in some cases improve separation. Although they may be colored or radioactive, and hence detectable without any sort of activation, they preferably are activatable. For example, dyes which fluoresce are particularly preferred. One exemplary agent is Primulin (3-galactoside hemihende cahydrate) (Direct Yellow 59), which can be activated by ultraviolet (UV) light. Primulin-dyed lipids are non-reactive for several days, affording later analysis, if necessary. The Primulin-stained lipid bands can be outlined on the silica TLC plate with a light pencil and scraped for extraction and further analysis. The UV light can be provided by a laser or other conventional light source. Other non-destructive dyes include ninhydrin, fluorescamine and iodine.

If further analysis is not done, however, destructive dyes may be used. Those well known to the chemist include molybdenum-sulfuric acid and recorsinol.

Quantification

Due to the exceptional separation capabilities of the present system, it is particularly useful in quantitative methods. Quantification may be performed in situ on the TLC plate, or the target molecule may be removed from the TLC medium by suitable means. Useful quantitative methods are widely available in the art and include ultraviolet-visible spectrophotometry, mass spectroscopy, liquid scintillation, autoradiography, photography (analog and digital, including video), and fluorimetry.

Additionally, immunoassays may be utilized. Typically, these immunoassays utilize an antibody having specificity for the target molecule. The primary, target-specific antibody, is bound to the lipid and the conjugate formed is detected, either directly or indirectly. Indirect detection can be accomplished using a secondary antibody which is specifically bound to the primary antibody. A means for facilitating detection can be attached either to the primary, target-specific, antibody or to the secondary antibody. These can include a radioactive label, a conjugated enzyme, and any other chemical or physical moiety that is detectable using standard techniques. The resulting antibody complex can be detected using, for example, liquid scintillation or autoradiography. If the an enzyme is used, the products of the enzymatic reaction can be detected using, for example, UV-visible spectroscopy, fluorimetry or photographic film.

The actual amounts of target molecule can be determined using a number of different methods. One method involves integration of the chromatogram peaks that result from the above methods. The area of these peaks is directly related to the level of target molecule present in the sample. Thus, the area of the peak represents a quantity that can be used to compare relative levels of target molecules. By analyzing fixed amounts of known target species, the exact relationship of peak area to target concentration can be determined. This relationship can be used to determine the concentration of target molecule in a sample.

Another method is based on the signal strength from the detection means. In general, the strength of this signal is directly proportional to the concentration of the target species present in the sample. Thus, using known concentrations of standards, a numerical value can be assigned to this relationship. This information can be used to determine the concentration of target molecule present in a sample.

Further Manipulation

Because of the incorporation of non-destructive detection techniques, it is possible to use the invention for isolating quantities of the target molecule for further analysis. For example, once separation is effected, the molecule can be removed from the TLC plate by scraping the area in which the molecule is detected. Following conventional extraction techniques, the molecule can be transferred into a suitable medium for further structural analysis.

The lipids thus extracted may be hydrolyzed and/or derivatized to facilitate subsequent detection and separation. In most cases, further structural analysis can still be performed, as long as the hydrolysis and/or derivatization does not disrupt the structural integrity of the portion of interest. One exemplary derivatization is the formation of fatty acid methyl esters.

This further analysis can include all manner of additional chromatography or spectrography in conjunction with the appropriate chemical treatments. For example, the nature of lipid acyl side chains can be determined by hydrolysis and subsequent analysis on, for example, a gas chromatograph (GC) and/or mass spectrometer (MS). Some typical derivatizations and further analyses can be found in Camacho et al. J. Biol. Chem. 270:17279–86 (1995) and Major et al., J. Chromatog. 658:233–40 (1994), both of which are hereby incorporated by reference.

EXAMPLES

Reagents: Standard lipids were purchased from Avanti Polar (Alabaster, Ala.); these included cholesteryl ester (CE), triacylglycerol (TAG), free fatty acid (FFA), diradylglycerol (DG), cholesterol (Chol), monoacylglycerol (MAG), phosphatidyl ethanolamine (PE), phosphatidyl choline (PC), phosphatidyl serine (PS), phosphatidyl inositol (PI), and phosphatidic acid (PA) as well as the various lysophospholipids. 14C-labeled PE, PC, PA, and Oleic acid standards were purchased from Amersham (Arlington Heights, Ill.), and $^{14}C$ labeled CE, TAG, DG, Chol, and MAG were purchased from American Radiolabeled Chemicals, Inc. (St. Louis, Mo). Chloroform, methanol, hexane, ether, and acetone of HPLC grade were obtained from Burdick & Jackson (Muskegon, Mich.). Acetic acid, and ammonium hydroxide were purchased from J. T. Baker (Phillipsburg, N.J.). Normal phase silica gel high performance TLC (HPTLC) plates (20×20 cm), with organic binder and UV254 indicator preincorporated, were purchased from Analtech (Newark, Del.). Primulin dye (C.I. 49000; Direct Yellow 59) was obtained from Sigma Chemical Co. (St. Louis, Mo.). Preval TLC sprayer was purchased from Precision Valve Corporation (Yonkers, N.Y.). Fluorescent analysis was carried out on a STORM 840 imaging system, Molecular Dynamics (Sunnyvale, Calif.). ECV.304 cells, a line derived from human umbilical vein endothelial cells, were obtained from ATCC (Rockville Md.). Cell culture reagents (Medium 199, PBS, Fetal Calf Serum, and trypsin) were obtained from Gibco BRL (Grand Island N.Y.). Human serum samples were prepared from clotted venous blood that had been obtained from normal volunteer subjects under an IRB-approved protocol.

Standard Lipid Mixtures: Mixtures of standard lipids were made up in the approximate ratios of lipids found in ECV.304 cell lipid extracts and serum lipid extracts as determined from previous experiments. The lipids in the standard cellular lipid mixture included (in $\mu$moles/ml): CE (0.5), TAG (1), FFA (0.5), DG (0.5), Chol (8), MAG (0.5), PE (2.5), PC (2.5), LPA (1), and PA (1). The lipids in the standard serum lipid mixture included (in $\mu$moles/ml): CE (4), TAG (4), FFA (2), DG (0.5), Chol (4), MAG (0.5). PI, PS, cer, glycolipids, steroids and other lyso-phospholipids were applied to TLC plates individually at single concentrations solely to determine their mobility in the two MOD-TLC systems.

Example 1

General and Methods

Growth of ECV.304 cells: ECV.304 cells were grown in T-175 tissue culture flasks containing Medium 199 with 10% fetal calf serum in a humidified incubator under an atmosphere of 5% $CO_2$/95% filtered room air at 37° C. The cells were passaged after mild trypsinization. Fifty-three 150 cm2 tissue culture plates were seeded with 1×105 cells in 25 ml of medium and grown under the same incubation conditions as for the cells in flasks. After two days, when the cells had reached approximately 85% confluence, they were washed twice by addition of 10 ml of PBS followed by aspiration of the fluid, before extraction of their lipid contents.

Cellular Lipid Extraction: Ten ml of ice-cold methanol containing 0.025% 2,6-Di-tert-butyl-methylphenol (butylated hydroxytoluene: BHT) was added to a cell culture plate and the cells were detached from the plate by scraping with a rubber spatula. The methanolic extract/cell suspension was recovered by aspiration with a 10 ml glass pipette and then added in succession to each of four additional culture plates before scraping the cells from each and aspirating the resulting suspension. Following the initial recovery of the aspirated methanolic suspension, the first plate was washed with an additional 10 ml of methanol, again aspirated to dryness, and the methanolic wash again transferred to wash each successive plate. The total volume of methanolic extracts, including washes from these 5 plates (20 ml), was pooled into a 50 ml glass tube. An additional 5 plates were extracted in the same manner and pooled into the same 50 ml glass tube, bringing the total volume to 40 ml. Forty additional cell culture plates were processed in groups of ten in the same manner, resulting in the collection of 5 separate pools of methanolic extract material.

The methanol extract/suspension was sonicated for 15 minutes in a bath sonicator at room temperature, Branson (Danbury, Conn.), followed by centrifugation at 1500×g for 10 minutes at room temperature. The supernatant was removed by aspiration with a glass pipette and dried under a stream of nitrogen at 37° C. The pellet was then re-extracted with 10 ml of chloroform:methanol:water (1:1:0.1, v/v/v), sonicated as above for 10 minutes and vortexed for 2 minutes. This extract was centrifuged for 10 minutes at 1500×g at room temperature and the supernatant added to the dried lipid extract of the original supernatant and again dried under a stream of nitrogen. The pooled, dried lipid extract was then partitioned by a modification of the Folch-Pi method (J. Biol. Chem. 191, 819–831 (1951)), by the addition of 12 ml of chloroform:methanol (C:M) (2:1, v/v) and 2 ml of 0.5M KCL/0.2N $H_3PO_4$. This mixture was sonicated at room temperature for 2 minutes, vortexed at room temperature for 2 minutes, inverted and shaken for 3 minutes, and then centrifuged for 10 minutes at 1500×g at room temperature. The upper phase was aspirated and discarded and the lower phase was dried under nitrogen stream at 37° C. and brought up in 1 ml of C:M (2:1, v/v) for application to TLC.

A separate set of three plates of ECV.304 cells was scraped in PBS and used to determine the protein concentration per plate of cells. Protein determination was carried out by the Bio-Rad Protein Assay, Bio-Rad Laboratories (Richmond Calif.). The total lipid content among extracts was normalized by calculating the ratio of nmoles lipid/mg cell protein.

Serum Extraction: To 2.5 ml of serum were added 2 ml of 2M KCl/0.2M $H_3PO_4$ and the solution was vortexed for 30 seconds. Next, 5.5 ml of C:M (2:1, v/v) was added and the mixture was vortexed for 2 minutes, sonicated for 30 seconds, and inverted rapidly 10 times, at room temperature. The sample was then centrifuged at 1000×g for 15 minutes at room temperature. The upper phase was removed, and the lower organic phase was evaporated to dryness by a nitrogen stream at 37° C. The dried lipid extract was resuspended in 0.5 ml C:M (2:1, v/v) for application to TLC.

Multi-One-Dimensional (MOD) TLC: Solvents for TLC were made in approximately 1 liter batches, mixed by vigorous shaking, and degassed by sonication for 5 minutes. TLC developing chambers, VWR-SP (Seattle Wash.), were lined with 3 mm chromatography paper, Whatman (Fairfield N.J.), on all sides. 125 ml of mixed degassed solvent was added to the TLC tank and allowed to equilibrate for two hours before the plates were run.

Fifty microliter Hamilton syringes were used to aspirate 2–50 μl portions of the lipid extracts and apply them to HP-TLC plates (20×20 cm), via a TLC Multi-Spotter, Analytical Instrument Specialties (Hernando Fla.). The samples were applied 2 cm from the bottom of the plates, at an approximate rate of 5 μl per minute with continuous application of warm air from a hair dryer. After the spots were fully dried, Multi-One-Dimensional Neutral TLC (MOD-Neutral TLC) was run as follows: First the plates were run to 5 cm from the bottom in chloroform-methanol-acetic acid (90:10:1, v/v/v) over approximately 3.5 minutes. The plates were then fully dried with a hair drier and run in hexane-diethylether-acetone (60:40:5, v/v/v) to 16 cm from the bottom, over approximately 21 minutes. Again, the plates were dried and then run in hexane-diethylether (97:3, v/v) to 19 cm, over approximately 32 min. Finally, the plates were dried and run to the top, plus an additional two minutes, in 100% hexane, with elapsed time for this final step of approximately 40 minutes.

Multi-One-Dimensional-Flip-Flop TLC (MOD-FF TLC): For Multi-One-Dimensional-Flip-Flop TLC (MOD-FF TLC), the samples were applied to HPTLC plates 6 cm from the bottom of the plates and otherwise processed by the same method as was used for MOD-TLC, except for the selection of mobile phase solvents and the running time for each. Thus, after drying of the applied samples, the plates were run in hexane:diethylether:acetone (60:40:5, v/v/v) to the top, over approximately 40 min. The plates were then dried and run in chloroform-methanol-ammonium hydroxide-water (60:35:4:1, v/v/v/v) to 18 cm, over approximately 60 min. After the plates were again dried, they were scored using a diamond pointed pencil with a rulers straight edge on the glass side of the TLC plate at 8.5 cm, just below the PC spot, followed by breaking apart with hand pressure. The line through which to cut the TLC plate was determined by visualizing and measuring the PC location on a different plate which was run in the same solvent system, or by spraying only the outside lane of the plate to be cut, which contained a PC standard spot. The lower portion, containing the points at which the samples were originally applied, was inverted (i.e., rotated by 180° and TLC was run in chloroform-methanol-acetic acid:water (85:12.5:12.5:3, v/v/v/v), from the edge created by breaking the original plate to the top of the plate in its inverted orientation (i.e., the bottom in the original orientation), over approximately 15 minutes.

Example 2

Detection, Identification and Quantification of Lipids

After completion of either type of TLC, the plates were dried by a hair drier and sprayed with a 0.05% solution of Primulin dye (a 1:100 dilution of a 5% aqueous stock into acetone-water, 8:2, v/v). The plates were sprayed in a uniform manner until just visibly moist, and then dried for 2 minutes with a hair dryer. Lipid spots were first visualized by a hand held UV lamp, UVL-21, UVP Inc. (San Gabriel, Calif.) in order to assess the quality of separation or to mark lipids for scraping and extraction. The plates were then scanned by laser-excited fluorescent detection on the STORM 840 (Molecular Dynamics) imaging system. Spots were quantified by integration of variable pixel intensities on Imagequant software (Molecular Dynamics) and compared to standard curves.

Verification of Mobility and Extraction Efficiency with $^{14}C$ standards: To 100 μl of ECV.304 cell extract was added, in separate tubes, 1 μC $^{14}C$ labeled plus 0.1 μmole unlabeled CE, TAG, Chol, MAG, PE, PC, PA, and Oleic acid standards. This mixture was then sonicated for 30 seconds and dried under a stream of nitrogen at 37° C. The dried lipids were then resuspended in 100 μl of C:M (2:1, v/v), 10 μl was spotted for each lane on the TLC plates, and chromatography was carried out by either the MOD-Neutral TLC or MOD-FF TLC system. After the chromatography procedures were run, both phosphoimages, and fluoroimages were recorded. Labeled spots were then marked and extracted from the silica, as below, and the percent extraction efficiency was determined by calculating the ratio of the radioactivity in the organic extract to the sum of the radioactivity remaining in the silica pellet plus that in the organic extract.

Example 3

Further Analysis

This example provides methods that are useful after the separation and detection in further analysis the target molecule. In this example, the identities of the acyl chains of certain target lipids were determined, as was the purity of target molecule that resulted from the inventive separation. Notably, mass spectral analyses revealed no contamination of one lipid class with another, supporting the quality of the separation obtained using the subject methods.

Extraction of Lipids From TLC Plates

Lipid spots were marked for extraction with a soft lead pencil after visualizing with the UV light. These marked areas were separately scraped from the silica plate with a razor blade and each portion of silica containing the lipid was placed into a 15 ml silanized glass tube. The silica was then extracted by the addition of 3 ml chloroform:methanol:water (1:1:0.1, v/v/v) followed by sonication at room temperature for three minutes and centrifugation at 1500×g at room temperature for five minutes. The supernatant was then removed by aspiration with a silanized glass pipette and placed in a 15 ml silanized glass tube. The pelleted silica was re-extracted as above, and the supernatant was pooled with that from the first extraction. The chloroform:methanol:water supernatant was then dried by a nitrogen stream at 37° C. In order to remove dissolved silica and Primulin, and to convert the acidic lipids from their salt forms to their acid forms, lipids were resuspended in 6 ml CM (2:1, v/v) and partitioned by the addition of 1 ml of 0.5 N hydrochloric acid (modified from Folch-Pi et al., supra). The organic lower phase was then aspirated with a silanized glass pipette, and the aspirate delivered to a 15 ml silanized glass tube, and dried under a nitrogen stream.

Fast-Atom Bombardment and Electrospray Mass Spectrometry (FAB/MS)

FAB/MS: spectra were acquired using a VG 70 SEQ tandem hybrid instrument of EBqQ geometry (VG Analytical, Altrincham, UK). The instrument was equipped with a standard unheated VG FAB ion source and a standard saddle-field gun (Ion Tech Ltd., Middlesex, UK) that produced a beam of xenon atoms at 8 KeV and 1 mA. The mass spectrometer was adjusted to a resolving power of 1,000 and spectra were obtained at 8 kV and at a scan speed of 10 sec/decade. 2-hydroxyethyl disulfide (2-HEDS) was used as matrix in the positive ion mode (FAB+), and triethanolamine was used as a matrix in the negative ion mode (FAB−). Bursten et al., J. Biol. Chem. 266, 20732–20743 (1991) and Bursten et al., Circulatory Shock 44, 14–29 (1994).

Electrospray MS and MS/MS: Electrospray MS and MS/MS (tandem) spectra were acquired using a VG Quattro II tandem triple quadropole mass spectrometer (Micromass, Manchester, UK) with information acquired and analyzed utilizing VG MassLynx, MaxEnt, and BioLynx software. Samples were dissolved in 300–400 μl $CH_3CN$ or $CH_3OH$, and then delivered by direct infusion via a Shimadzu LC-10AD liquid chromatograph pump (isocratic mobile phase 1:1 $CH_3CN:H_2O$) run at 50 μl/min, with 5 μl of sample injected into the electrospray capillary tip per analysis. Voltage of the cone was set at 27 eV, and of the capillary tip at 3800 V. The source temperature was set at 100° C. Data were acquired in centroid scan mode from m/z 105 to 1000 or 105 to 2000 in 2.5 sec scans.

Lipid Hydrolysis and Gas Chromatography of Fatty Acyl-Chains: Lipid hydrolysis and subsequent gas chromatography (GC) of released fatty acyl-chains was adapted from Major and Wolf (J. of Chromatography 658, 233–240 (1994)), with slight modifications to the GC analysis, in that a three meter deactivated fused silica retention gap was used in line between the injector and the analytical column. The column temperature program ran from 75° C. at injection to 160° C. linearly over 36 seconds and then to 250° C. linearly over 102 seconds. The pressure was set at 52 K Pascals. Lastly, the oven temperature program ran from an initial temperature of 75° C. to 165° C. linearly over 135 seconds and to 250° C. over 24.25 minutes. The oven was then held at 250° C. for 2 minutes. GC analysis was on a HP5890 series II Instrument, with a HP 19322 Electron Capture Detector; HP Chemstation was used for data analysis.

Example 4

Analysis of Lipids Using MOD-TLC

This example uses the foregoing methods to demonstrate the actual practice of the invention to analyze certain lipid target molecules.

Using the MOD-Neutral TLC system CE, TAG, FFA, DG, Chol, and MAG were separated to homogeneity from lipid extracts of cultured ECV.304 cells and pooled human sera, (FIG. 1 Panels A and B), and the phospholipids, PC, PE and PA, were separated using the MOD-FF TLC system from the same lipid extracts (FIG. 1 Panels C and D). The identities of these resolved lipids were confirmed in two ways: first by co-migration with $^{14}C$ labeled standards, and secondly by FAB/MS analysis of the resolved extracted lipids. By using $^{14}C$ labeled standards of the resolved lipids (FIG. 1 Panels B and D), we determined that for CE, TAG, FFA, Chol, MAG, PE, PC, and PA, >99.9% of the standard lipid migrated at a specific Rf value, separate from those of other lipids. There was no smearing of lipids on the TLC plate and none of the resolved lipid standards remained at the origin of spotting. After visualizing the resolved lipids with the aid of Primulin dye and a hand held UV light, each band was marked, scraped, and extracted from the silica. Using the $^{14}C$ labeled standards, we determined the extraction efficiency from silica to be >95% (+/−3%, for n=8). FAB/MS of the extracted lipids confirmed the identities of the resolved lipids co-migrating with the lipid standards (Table 1).

All phospholipids, sphingomyelin, and glycosphingolipids remained at or near the origin in the MOD-Neutral TLC system (FIG. 1 Panels A and B). In the MOD-FF TLC system the neutral lipids migrated to or near to the top of the TLC plate (FIG. 1 Panels C and D). Some glycosphingolipids, namely ceramide mono-hexose (CMH), migrate above PE and below FFA in the MOD-FF TLC system (FIG. 1 Panel C); these glycosphingolipids could be specifically visualized with Orcinol charring. Nunelman et al., J. Biol. Chem 261, 5487–5495 (1986). Other glycosphingolipids, lysophospholipids, sphingomyelin, as well as the glycerol phospholipids PI and PS migrated between the origin and PA, in the MOD-FF TLC system (FIG. 1 Panel C). PA was the fastest migrating lipid in the mobile phase solvent used after rotating the plate in FF-TLC; it was easily resolved from all other lipids for quantification or extraction.

Figure 1A:
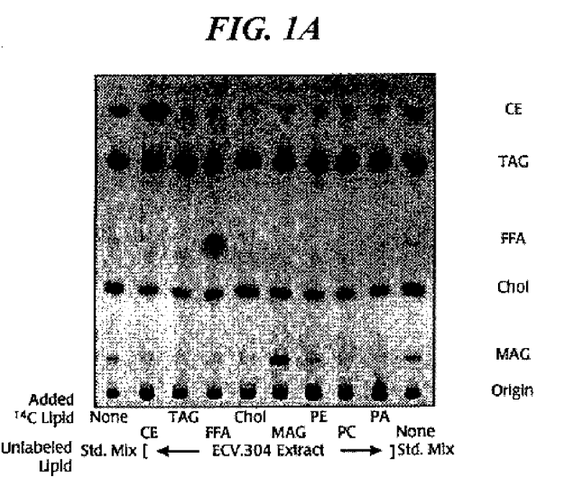
FIGS. 1A and 1B show separations using lipid extracts of cultured ECV.304 cells and standard lipids, respectively, on MOD-TLC (MOD-Neutral TLC).
Figure 1B:
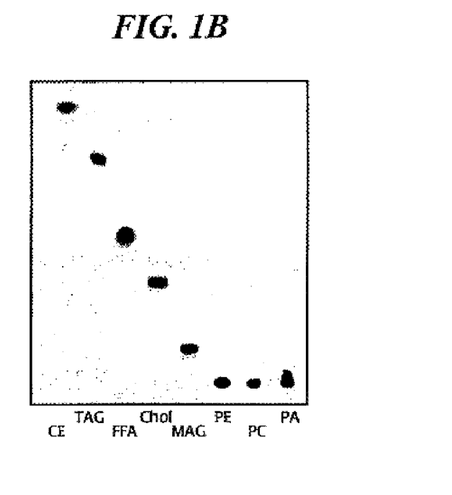
Figure 1C:
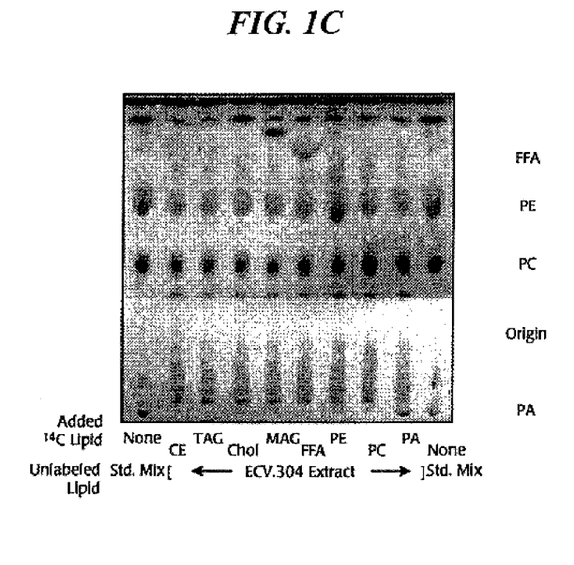
FIGS. 1C and 1D show the same separations using MOD-FF TLC.
Figure 1D:
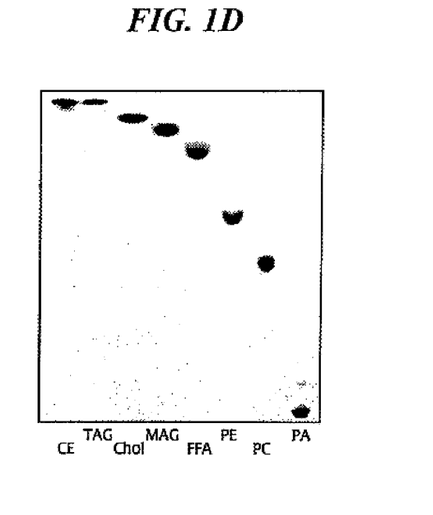
Figure 2A:
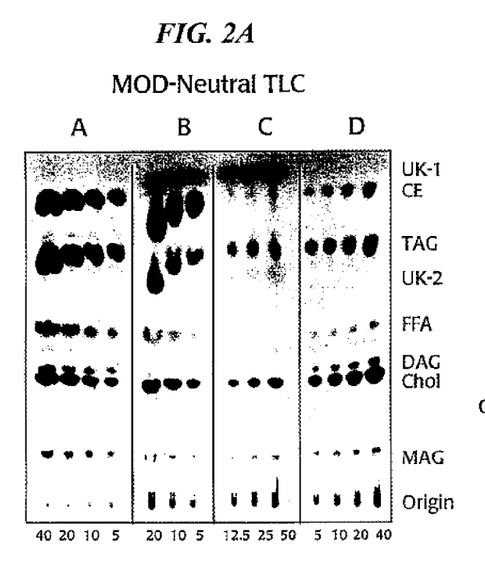
FIGS. 2A and 2B illustrate the separation of standard lipids and sera using MOD-Neutral (FIG. 2A) and MOD-FF TLC (FIG. 2B). Lanes A and D–G contain standard lipids. Lane B contains pooled sera and lane C contains lipids from ECV.304 cells.
Figure 2B:
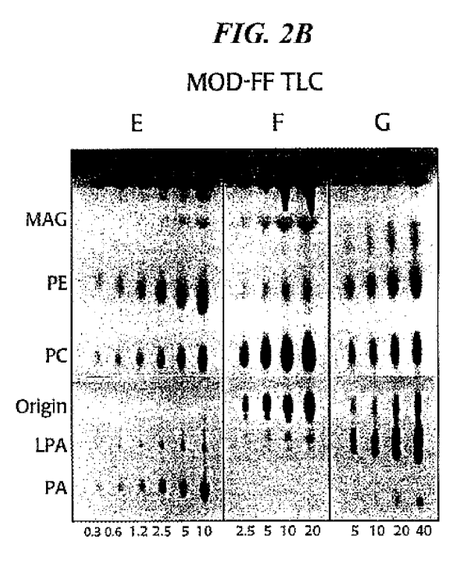
Figure 3:
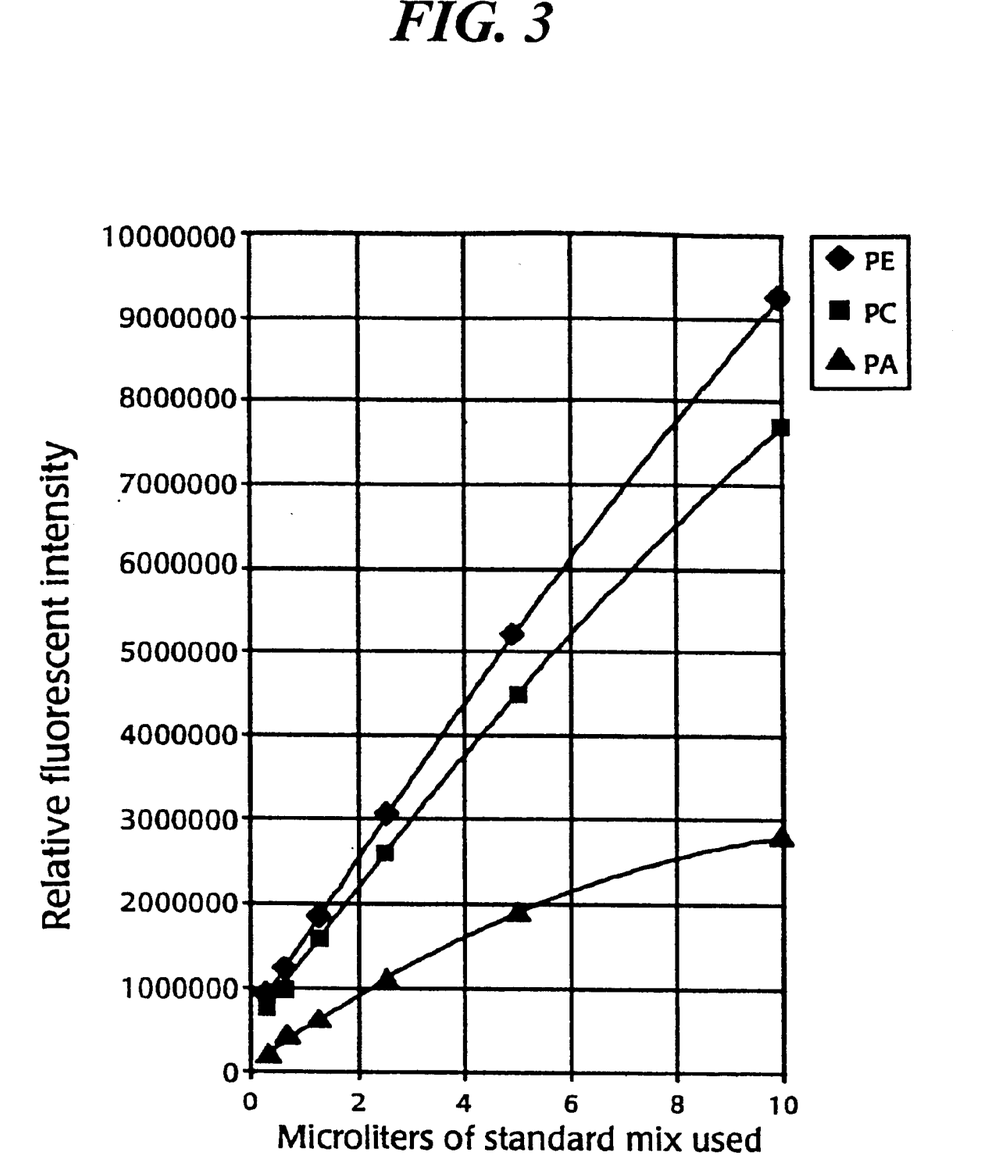
FIG. 3 shows representative curves generated by conducting STORM analysis of the serially diluted standard lipids from lane E of FIG. 2.

In order to quantify the extracted lipids of ECV.304 cells and human sera, dilution curves were made on TLC plates of the lipid extracts and known standards (FIG. 2). By comparing the pixel intensity curves generated from the STORM analysis of the serially diluted standard lipids (for example FIG. 3, generated from panel E of FIG. 2) to the dilution curves of the extracted lipids of ECV.304 cells and human sera (FIG. 2 panels B, C, F, and G), we were able to interpolate the lipid concentrations of the lipid extracts (Table 2). To accurately quantify the PA in human serum and ECV.304 cell lipid extracts, the total lipid extracts were applied to TLC plates in quantities at least 20-fold greater than those shown in FIG. 2, panels F and G. The lipid concentrations determined by this TLC analysis of human sera fell within the normal ranges of "Reference Intervals and Laboratory Values of Clinical Importance" as reported in CECIL TEXTBOOK OF MEDICINE (Saunders 1988). From unstimulated ECV.304 cells, the PA/PC ratio of 4.6%, the DG/PC ratio of 3.3%, and the PA/DG ratio of 1.4 (Table 2), are in accord with historical ranges, Izmailov et al., Farmatsiya 3, 1 (1938), although no previous reports on lipid analyses of endothelial cell extracts are available for comparison. Similarly, the PA/PC ratio of 0.6% in serum also represents a good correspondence with historical data. Wyngaarden et al., in CECIL TEXTBOOK OF MEDICINE, supra. By the analysis of several different thin layer chromatograms and by the repeated spotting of several different standard lipids on the same TLC plate, we have determined the intra-assay variation to be 6% (n=9), and the inter-assay variation to be 8% (n=5) for the quantification of lipids by this method.

Using the STORM laser-activated fluorescent detection system, we were able to quantify, by pixel intensity, the amounts of each lipid in the total extracts of serum or cells, based upon standard curves. The sensitivity of this analysis is in the picomolar range and does not rely on the pre-labeling of cells (i.e. for generation of radiolabled lipids) or the use of destructive dyes for detection.

Different standard curves for the quantification of lipid extracts from sera versus cultured cells were used, since the lipids are present in different proportions in these extracts and we wished to match those proportions for accurate quantitation. The intra-assay and inter-assay standard deviations were relatively small (6%–8%). Since we were able to use $^{14}C$ labeled standards to determine extraction and separation efficiencies, we are confident that all (>99.9%) of the isolated lipids are present at their designated locations on the TLC plates and that >95% of all lipid can be extracted from silica for further analysis.

To demonstrate the utility of this MOD TLC system as well as to generate a baseline of acyl chain compositions of lipids in unperturbed cultured ECV.304 cells for further experiments, we determined the acyl chain compositions of the resolved extracted lipids. Separated lipids were extracted from marked silica spots and hydrolyzed. The released acyl chains were analyzed by gas chromatography and compared to known standards. Table 3 shows the percentage of individual species of acyl chains greater than 2% found in CE, TAG, DG, FFA, and PA of cultured ECV.304 cells. The data illustrate the usual concordance between DG and TAG acyl chain content (due to the origin of TAG from the DG pool), with enrichment in the non-arachidonate polyunsaturated fatty acids (e.g., 22:3 and 22:6). Of further note is the composition in ECV.304 cell lipid extract free fatty acids, which shows predominance in the palmitate (16:0), stearate (18:0), and oleate (18:1), with less representation from linoleate (18:2) than is usual. See Bursten et al., J. Biol. Chem 266, 20732–20743 (1991). Finally, the acyl composition of PA in these unstimulated cells is found to be highly saturated (palmitate+stearate=55%) and monounsaturated (oleate=33%), which is consistent with our previous determinations of resting cell PA. Id.; Bursten et al., Cell Physiol. 35, C1093–C1104 (1994); and Wen et al., Amer. J. Physiol 269 (Cell Physiol 38) C435–C442 (1995).

The foregoing detailed description and examples are merely illustrative of the preferred embodiments. They are by no means meant to be the exclusive description of the inventive concept hereby disclosed. It will be recognized by one of ordinary skill in the art that certain aspects of the practice of the invention are readily susceptible to modification or practice by alternative, known means.

TABLE 1

Mass Spectrometry of Lipids Isolated From ECV.304 Cells

| Lipid | Analysis | Molecular Ion | Species |
| --- | --- | --- | --- |
| CE | FAB (+) | 648 | 18:2 |
|  |  | 676 | 20:2 |
| TAG | FAB (+) | 856 Na Adduct | 16:0/16:0/18:0 |
|  |  | 884 Na Adduct | 16:0/18:0/18:0 |
|  |  | 912 Na Adduct | 18:0/18:0/18:0 |
|  |  | 940 Na Adduct | 18:0/20:0/18:0 |
| DAG | FAB (+) | 604 | 18:0/18:1 |
|  |  | 578 | 16:0/18:1 |
|  |  | 550 | 16:0/16:1 |
| MAG | Electrospray | 359 (+) | 18:0 |
|  |  | 381 (+) Na Adduct |  |
| FFA | FAB (−) | 283 | 18:0 |
|  |  | 281 | 18:1 |
|  |  | 255 | 16:0 |
| PE | FAB (+) | 745 | 18:0/18:1 |
|  |  | 743 | 18:0/18:2 |
|  |  | 775 | 18:0/20:0 |
| PC | FAB (+) | 733 | 14:0/18:1 |
|  |  | 761 | 16:0/18:1 |
|  |  | 787 | 18:1/18:1 |
| PA | FAB (−) | 647 | 14:0/18:1 |
|  |  | 673 | 16:0/18:1 |
|  |  | 701 | 18:0/18:1 |

TABLE 2

Concentration of Lipids in ECV.304 Cells and Human Sera (N = 5)

| Lipid | nMoles lipid/mg ECV cell protein | nMoles lipid/mL sera |
| --- | --- | --- |
| CE | 58 +/− 2 | 2500 +/− 100 |
| TAG | 37 +/− 1 | 840 +/− 40 |
| FFA | 3 +/− 0.2 | 240 +/− 10 |
| DAG | 5 +/− 0.2 | 14 +/− 0.6 |
| Chol | 166 +/− 6 | 740 +/− 30 |
| MAG | 6 +/− 0.5 | 38 +/− 2 |
| PE | 163 +/− 7 | 76 +/− 3 |
| PC | 154 +/− 5 | 1460 +/− 50 |
| PA | 7 +/− 0.3 | 9 +/− 0.3 |

TABLE 3

% of acyl chains in lipid species of ECV.304 cells (SD = +/−8%, n = 4) ((<) indicates less than 2%)

| acyl chain | CE | TAG | DAG | FFA | PA |
|---|---|---|---|---|---|
| 14:0 | 4.3 | 3.0 | 3.3 | 5 | 2.8 |
| 16:0 | 21 | 17 | 20 | 36 | 22 |
| 16:1 | 7.7 | 2.8 | 2.9 | (<) | (<) |
| 18:0 | 2.2 | 8.2 | 11 | 32 | 33 |
| 18:1 | 47 | 35 | 36 | 17 | 33 |
| 18:2 | 9.1 | 4.4 | 4.8 | 6.2 | 2 |
| 18:3 | (<) | (<) | 7.5 | (<) | (<) |
| 18:3t | (<) | 4.9 | 2.1 | (<) | (<) |
| 20:4 | 4.1 | 2.8 | 4.2 | (<) | 3.3 |
| 22:3 | (<) | 4.7 | 2 | (<) | (<) |
| 22:6 | (<) | 6.4 | 2.2 | (<) | 5 |

We claim:

1. A method of separating and detecting a target molecule, comprising:

(a) providing a sample which contains said target molecule;

(b) separating said target molecule by thin layer chromatography (TLC), wherein said TLC comprises resolving said sample in one direction in one dimension, followed by resolving said sample at least a second time in the same dimension, wherein the mobile phase in said first resolution comprises chloroform-methanol-acetic acid/ammonium hydroxide and the mobile phase of said second resolution comprises a solvent mixture selected from the group consisting of hexane-diethylether-acetone, hexane-diethylether and 100% hexane; and (c) detecting said separated target molecule.

2. The method of claim 1, wherein said chloroform-methanol-acetic acid/ammonium hydroxide mobile phase contains at least about 80% (v/v/v) chloroform, said hexane-diethylether-acetone mobile phase contains at least about 55% hexane (v/v/v) and said hexane-diethylether mobile phase contains at least about 93% (v/v) hexane.

3. The method of claim 2, comprising repeating said second resolution at least two more times, each time in a different mobile phase.

4. The method of claim 3, wherein said chloroform-methanol-acetic acid/ammonium hydroxide mobile phase contains at between about 86% and about 94% (v/v/v) chloroform, said hexane-diethylether-acetone mobile phase contains between about 57% and about 63% hexane (v/v/v) and said hexane-diethylether mobile phase contains between about 91% and about 95% (v/v) hexane.

5. The method of claim 3, wherein said chloroform-methanol-acetic acid/ammonium hydroxide mobile phase contains between about 8% to about 12% (v/v/v) methanol, said hexane-diethylether-acetone mobile phase contains between about 35% and about 45% diethylether (v/v/v) and said hexane-diethylether mobile phase contains between about 1% and about 7% (v/v) diethylether.

6. The method of claim 5, wherein said chloroform-methanol-acetic acid/ammonium hydroxide mobile phase is 90:10:1 (v/v/v), said hexane-diethylether-acetone mobile phase is 60:40:5 (v/v/v) and said hexane-diethylether mobile phase is 97:3 (v/v).

7. The method of claim 1, wherein said target molecule is selected from the group consisting of a lipid, a lipoprotein, a phospholipid, a glycolipid, a glycerol lipid, a sulfolipid, a sphingolipid, a steroid, a lipid soluble vitamin, a peptide, an amino acid, an oligosaccharide and a methylxanthine.

8. The method of claim 7, wherein said detecting comprises exposing the separated lipid to a non-destructive dye.

9. The method of claim 8, wherein said dye is 3-galactoside hemihendecahydrate.

10. The method of claim 8, wherein said detecting further comprises illuminating the lipid with ultraviolet light.

11. The method of claim 8, wherein said detecting further comprises illuminating the lipid with laser light.

12. The method of claim 7, further comprising determining the structural identity of the separated lipid.

13. The method of claim 12, wherein said determining comprises hydrolyzing an acyl chain of said separated lipid and identifying said acyl chain.

14. The method of claim 7, further comprising quantifying the amount of the separated lipid.

15. The method of claim 7, wherein said lipid is a phosphatidic acid (PA) or diradylglycerol (DG) species.

16. The method of claim 7, wherein said lipid is physiologically associated with the activity of an enzyme selected from the group consisting of lyso-PA acyl CoA acyltransferase (LPAAT), phosphatidate phosphohydrolase (PAP or PAPH), diacylglycerol kinase (DG kinase), protein kinase C and phosphatidylcholine-directed phospholipase D (PC-PLD).

17. The method of claim 7, wherein said lipid is selected from the group consisting of phosphatidyl glycerol, cardiolipin, cholesterol, cholesteryl ester (CE), triacylglycerol (TAG), free fatty acid (FFA), diradylglycerol (DG), cholesterol (Chol), monoacylglycerol (MAG), phosphatidyl ethanolamine (PE), phosphatidyl choline (PC), phosphatidyl serine (PS), phosphatidyl inositol (PI), phosphatidic acid (PA) and a lysophospholipid derivative thereof.

18. The method of claim 1, wherein said sample comprises a bodily fluid.

* * * * *